United States Patent
Tegg

(10) Patent No.: US 8,744,599 B2
(45) Date of Patent: Jun. 3, 2014

(54) HIGH DENSITY MAPPING CATHETER

(75) Inventor: Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1018 days.

(21) Appl. No.: 12/045,385

(22) Filed: Mar. 10, 2008

(65) Prior Publication Data

US 2008/0228060 A1 Sep. 18, 2008

Related U.S. Application Data

(60) Provisional application No. 60/894,144, filed on Mar. 9, 2007.

(51) Int. Cl.
*A61N 1/00* (2006.01)
*A61B 5/04* (2006.01)
*A61B 18/18* (2006.01)

(52) U.S. Cl.
USPC .............................. 607/122; 600/374; 606/41

(58) Field of Classification Search
USPC ................. 600/466, 481, 483, 486, 374, 381; 606/41; 607/122, 123
See application file for complete search history.

(56) References Cited

U.S. PATENT DOCUMENTS

| | | | |
|---|---|---|---|
| 4,522,212 A * | 6/1985 | Gelinas et al. | 600/374 |
| 4,777,955 A | 10/1988 | Brayton et al. | |
| 5,133,365 A | 7/1992 | Heil, Jr. et al. | |
| 5,279,299 A | 1/1994 | Imran | |
| 5,309,910 A | 5/1994 | Edwards et al. | |
| 5,462,545 A | 10/1995 | Wang et al. | |
| 5,471,982 A * | 12/1995 | Edwards et al. | 600/374 |
| 5,509,419 A | 4/1996 | Edwards et al. | |
| 5,551,426 A | 9/1996 | Hummel et al. | |
| 5,582,609 A | 12/1996 | Swanson et al. | |
| 5,617,854 A | 4/1997 | Munsif | |
| 5,626,136 A | 5/1997 | Webster, Jr. | |
| 5,728,143 A * | 3/1998 | Gough et al. | 607/101 |
| 5,782,239 A * | 7/1998 | Webster, Jr. | 600/374 |
| 5,827,276 A * | 10/1998 | LeVeen et al. | 606/41 |
| 5,855,576 A | 1/1999 | LeVeen et al. | |
| 5,871,443 A | 2/1999 | Edwards et al. | |
| 5,876,336 A * | 3/1999 | Swanson et al. | 600/374 |
| 5,916,158 A * | 6/1999 | Webster, Jr. | 600/374 |
| 5,938,694 A | 8/1999 | Jaraczewski et al. | |
| 6,052,607 A | 4/2000 | Edwards et al. | |
| 6,071,280 A | 6/2000 | Edwards et al. | |
| 6,163,716 A | 12/2000 | Edwards et al. | |
| 6,669,693 B2 | 12/2003 | Friedman | |
| 6,997,925 B2 * | 2/2006 | Maguire et al. | 606/41 |
| 7,089,045 B2 | 8/2006 | Fuimaono et al. | |
| 7,099,712 B2 * | 8/2006 | Fuimaono et al. | 600/374 |

* cited by examiner

*Primary Examiner* — Linda Dvorak
*Assistant Examiner* — Brian M Antiskay
(74) *Attorney, Agent, or Firm* — Marsh Fischmann & Breyfogle, LLP

(57) ABSTRACT

The present invention is directed to a high density mapping catheter including a number of shape memory electrode fibers and associated methods of construction and operation. The invention ensures good electrical contact between a large number of mapping electrodes and cardiac tissue in relation to a number of cardiac tissue approach angles, including head-on approaches. In addition, the invention allows for a reduced range of deflection angles in relation to deployment and retraction of the electrode fibers, thereby reducing resistance to retraction and reducing stress on the fibers and associated concerns regarding patient safety. The catheter of the present invention allows for rapid acquisition of a large amount of mapping data and allows for a variety of different geometries in relation to sweeping of the catheter across the cardiac tissue.

23 Claims, 11 Drawing Sheets

HIGH DENSITY MAPPING CATHETER

CROSS REFERENCE TO RELATED APPLICATION

This application claims priority under 35 USC 119 to U.S. Provisional Application No. 60/894,144, entitled, "HIGH DENSITY MAPPING CATHETER," filed on Mar. 9, 2007, the contents of which are incorporated herein as if set forth in full.

BACKGROUND OF THE INVENTION a. Field of the Invention

The present invention relates to electrical mapping of a patient's heart and, in particular, to a catheter that can quickly gather data for high resolution cardiac mapping and associated methodology.

b. Background

A number of mapping and navigation options have been developed to enable electrical mapping of a patient's heart as well as navigation of an instrument, such as an electrode catheter, to a desired site for ablation or other treatment. For example, the EnSite NavX® utility is integrated into the Ensite® Advanced Mapping System by St. Jude Medical, Inc., and provides non-fluoroscopic navigation of conventional electrophysiology catheters. The navigation methodology is based on the principle that when electrical current is applied across two surface electrodes, a voltage gradient is created along the axis between the electrodes. Although any suitable number of electrodes may be utilized, typically six surface electrodes are placed on the body of the patient and in three pairs: anterior to posterior, left to right lateral, and superior (neck) to inferior (left leg). The three electrode pairs form three orthogonal axes (X-Y-Z), with the patient's heart being at least generally at the center.

The noted six surface electrodes are connected to the Ensite® Advanced Mapping System, which alternately sends an electrical signal through each pair of surface electrodes to create a voltage gradient along each of the three axes, forming a transthoracic electrical field, Conventional electrophysiology catheters may be connected to the Ensite® Advanced Mapping System and advanced to the patient's heart. As a catheter enters the transthoracic field, each catheter electrode senses voltage, timed to the creation of the gradient along each axis. Using the sensed voltages compared to the voltage gradient on all three axes, the EnSite NavX® utility calculates the three-dimensional position of each catheter electrode. The calculated position for the various electrodes occurs simultaneously and repeats many times per second (e.g., about 93 times per second).

The Ensite® Advanced Mapping System displays the located electrodes as catheter bodies with real-time navigation. By tracking the position of the various catheters, the EnSite NavX® utility provides non-fluoroscopic navigation, mapping, and creation of chamber models that are highly detailed and that have very accurate geometries. In the latter regard, the physician sweeps an appropriate catheter electrode across the heart chamber to outline the structures by relaying the signals to the computer system that then generates the 3-D model. This 3-D model may be utilized for any appropriate purpose, for instance to help the physician guide an ablation catheter to a heart location where treatment is desired/required.

In order to generate an accurate and highly detailed map of a patient's heart, a large amount of data is required. Accordingly, an electrode catheter may be swept across various surfaces of the heart while obtaining data as described above. In order to accelerate this mapping data acquisition and/or increase the volume of data available for mapping, a number of high-density electrode catheters have been developed or proposed. Generally, these include a number of electrodes in an array in relation to a catheter body so as to substantially simultaneously obtain many mapping data points for a corresponding surface of cardiac tissue proximate to the catheter body. For example, these electrodes may be deployed along the length of a section of the catheter body that has a coil or other three-dimensional configuration so as to provide the desired spatial distribution of the electrodes. Alternatively, the electrodes may be disposed on a number of structural elements extending from a catheter body, e.g., in the form of a basket or a number of fingers. Work continues towards developing a high density mapping electrode catheter that achieves the goal of rapidly gathering mapping information while being safe in operation and simple in construction.

BRIEF SUMMARY OF THE INVENTION

The present invention is directed to a high density mapping catheter including a number of shape memory electrode fibers and associated methods of construction and operation. The invention ensures good electrical contact between a large number of mapping electrodes and cardiac tissue in relation to a number of cardiac tissue approach angles, including head-on approaches. In addition, the invention allows for a reduced range of deflection angles in relation to deployment and retraction of the electrode fibers, thereby reducing resistance to retraction and reducing stress on the fibers and associated concerns regarding patient safety. The catheter of the present invention allows for rapid acquisition of a large amount of mapping data and allows for a variety of different geometries in relation to sweeping of the catheter across the cardiac tissue.

In accordance with one aspect of the present invention, a high density mapping catheter includes a plurality of thin forwardly extending electrode fibers. In this regard, the catheter includes a catheter body and a number of electrode filaments/fibers that extend from the catheter body. Free ends of these fibers extend forwardly towards the distal tip of the catheter body. Each electrode fiber supports at least one electrode thereon. In one arrangement, such electrodes are disposed on the distal ends of the fibers.

In one arrangement, each electrode fiber is formed as an elongated body. In such an arrangement, each filament has a proximal end that is attached to the catheter body and a free distal end. In one arrangement, the fibers comprise a substantially cylindrical body in an undeflected state. In such an arrangement, an angle between a long axis of the cylindrical body and the longitudinal axis of the catheter body may be an acute angle. In one arrangement, such an acute angle is between about 30° and about 60°.

In one arrangement, the distal ends of at least a portion of the electrode fibers extend to an axial location that is beyond the distal tip of the catheter body. In this regard, when the distal tip of the catheter is advanced axially forward, one or more of the distal ends of the electrode fibers may contact patient tissue prior to the distal tip of the catheter body contacting such tissue. In a further arrangement, all the distal ends of the fibers extend beyond the distal tip of the catheter body. Furthermore, in such an arrangement, all the distal ends may be disposed in a substantially common plane.

In one arrangement, the electrode fibers may be formed of a shape memory fiber having a remembered shape. In such an arrangement, such a shape memory fiber may further include a conductive core, which may function as an electrical pathway for one or more electrodes supported by the electrode fiber. In such an arrangement, the fiber may further include an insulative coating disposed over an outside surface of at least a portion of the conductive core. Furthermore, in such an arrangement, the electrode(s) may be integrally formed with the conductive core.

In one arrangement, the diameter of the catheter body is at least five times the diameter of each individual electrode fibers. In a further arrangement, the diameter of the catheter body is at least 10 times the diameter of such fibers. Correspondingly, each individual fiber may be no greater than about 0.006 inches in diameter or no greater than about 0.004 inches in diameter. In a further arrangement, an electrode disposed on the distal ends of the fibers may have a diameter that is greater than the diameter of the fiber supporting the electrode.

The fibers may be spaced about the circumference of the electrode body. In this regard, such spacing may be random or predetermined. In one arrangement, the plurality of fibers are disposed in at least three axial rows disposed around the circumference of the catheter. In any arrangement, the individual fibers may be staggered to reduce the likelihood of shorting when the fibers are deflected. Electrode fibers may in one arrangement each have a common length. In another arrangement, different electrode fibers attached to the catheter body may have different lengths.

In accordance with one aspect of the present invention, a high density mapping catheter is provided that utilizes thin electrode fibers. The catheter includes a catheter body and a number of fibers extending from the catheter body. The fibers have a width, along at least a portion of the length thereof that is no more than about 0.006 of an inch. In one implementation, fibers having a width of about 0.002 of an inch are utilized. At least one electrode is supported on each of the fibers for use in acquiring mapping information. For example, an electrode may be disposed at the tip of the fiber. In one embodiment, the fibers are formed from conductive core shape memory alloy wires. The electrode can be formed as a ball of the core material at the end of the fiber.

In accordance with another aspect of the present invention, high density mapping catheter includes a large number of electrode fibers. More specifically, the catheter includes a catheter body and at least about 16 electrode fibers extending from the catheter body. Each of the electrode fibers includes at least one electrode for use in acquiring mapping information. In this manner, a large amount of mapping information can be rapidly acquired, and mapping information can be acquired in connection with a variety of catheter/tissue geometries.

In accordance with yet another aspect of the present invention, different length electrode fibers are used in connection with a high density mapping catheter. The catheter includes a catheter body and a number of mapping electrode elements extending from the catheter body, where each of the elements is formed from a conductive core shape memory fiber. The elements include a first element and a second element where the first element has a length different than that of the second element. For example, such differing lengths may allow for a desired spatial configuration of the tip electrodes of the various fibers when unconstrained.

In accordance with another aspect of the present invention, a method is provided for use in constructing a high-density mapping catheter. The method involves providing a shape memory fiber with a conductive core. An end portion of the shape memory material of the fiber is then stripped back to expose the conductive core. The exposed portion of the conductive core can then be melted to form a generally spherical tip electrode. For example, the core may be melted by a laser or by exposure to another heat source. This allows for simple construction of electrode fibers having an enlarged rounded tip. Such a tip shape is desirable to avoid puncturing tissue and to enhance visibility of the tip electrodes in relation to various visualization modalities.

In accordance with a further aspect of the present invention, a method is provided for use in mapping cardiac tissue. The method includes the steps of: providing an electrode catheter, including a catheter body with a number of electrode elements extending therefrom, where each of the element is formed from a shape memory fiber having a conductive core, and the electrode catheter further includes a sheath; introducing the electrode catheter into a chamber of a patient's heart to be mapped; extending the catheter body from the sheath such that the mapping electrode elements extend from the catheter body in a mapping configuration; and sweeping the mapping electrode elements across a cardiac surface. The noted method allows for acquisition of a large volume of mapping information in a short time.

In accordance with another aspect of the present invention, a further method for use in mapping cardiac tissue is provided. The method involves providing an electrode catheter including a catheter body having a tip electrode disposed on a distal end thereof and a number of mapping electrode elements extending from the catheter body. Each of the mapping electrode elements is formed from a shape memory fiber having a conductive core. The method further involves operating a number of the mapping electrode elements, disposed circumferentially around the catheter tip electrode to obtain position information, and substantially simultaneously operating the catheter tip electrode to perform a desired medical procedure. For example, the catheter tip electrode may be a mapping electrode, and the medical procedure may involve mapping using the catheter tip electrode and the mapping electrode elements. Alternatively, the catheter tip electrode may be an ablation electrode, and the desired medical procedure may be an ablation procedure. In this regard, the mapping electrode elements may be used to guide the ablation electrode to the desired site or locus of ablation points.

DETAILED DESCRIPTION

Figure 1:
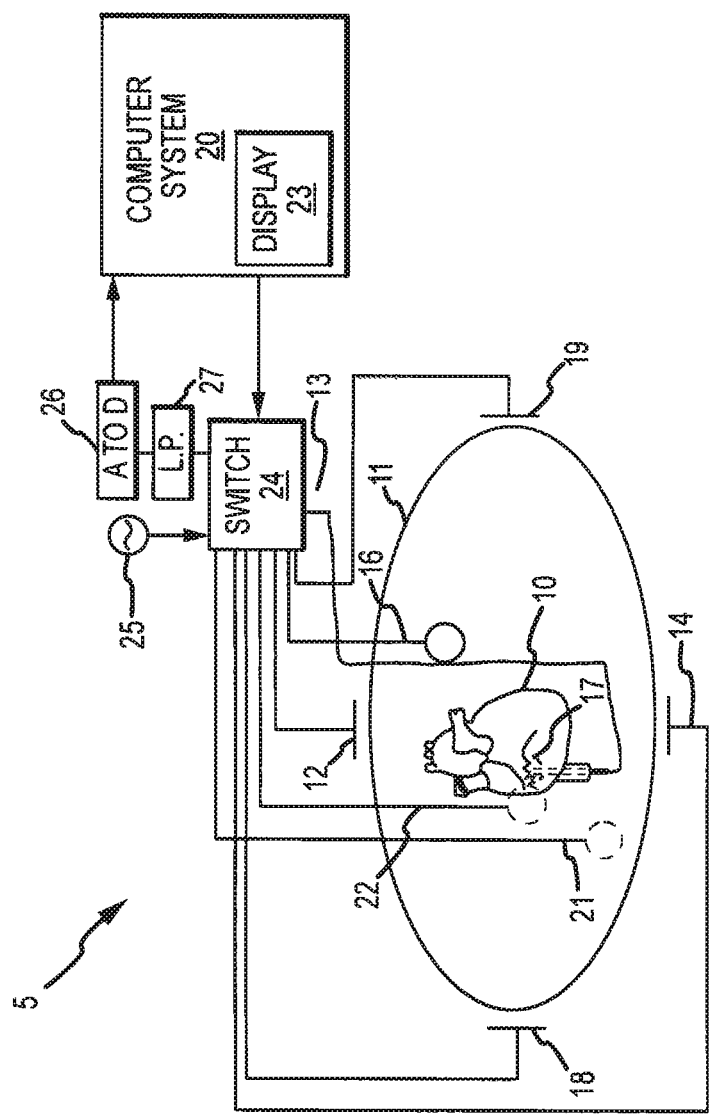
FIG. 1 is a schematic diagram of a navigation and mapping system in accordance with the present invention.

FIG. 1 presents a schematic of one embodiment of a medical navigation/visualization system 5. The medical navigation/visualization system 5 will be briefly addressed herein, as it is one such system that may utilize the mapping electrode functionality that will be addressed in detail below. The medical navigation/visualization system 5 is also discussed in detail in U.S. Patent Application Publication No. US 2004/0254437, that is entitled "METHOD AND APPARATUS FOR CATHETER NAVIGATION AND LOCATION AND MAPPING IN THE HEART," that published on Dec. 16, 2004, that is assigned to the assignee of this patent application, and the entire disclosure of which is incorporated by reference in its entirety herein.

The patient 11 is only schematically depicted as an oval for clarity. Three sets of surface or patch electrodes are shown as 18, 19 along a Y-axis; as 12, 14 along an X-axis; and 16, 22 along a Z-axis, Patch electrode 16 is shown on the surface closest to the observer, and patch electrode 22 is shown in outline form to show its placement on the back of patient 11. An additional patch electrode, which may be referred to as a "belly" patch, is also seen in the figure as patch electrode 21. Each patch electrode 18, 19, 12, 14, 16, 22, 21 is independently connected to a multiplex switch 24. The heart 10 of patient 11 lies between these various sets of patch electrodes 18, 19, 12, 14, 16, 22. Also seen in this figure is a representative catheter 13 having a number of electrodes 17. The electrodes 17 may be referred to as the "roving electrodes" or "measurement electrodes" herein. In the embodiments described below, many electrodes on fiber elements are used for high-density mapping. It should be appreciated that in use the patient 11 will have most or all of the conventional 12 lead ECG system in place as well, and this ECG information is available to the system although not illustrated in the figure.

Each patch electrode 18, 19, 12, 14, 16, 22, 21 is coupled to the switch 24, and pairs of electrodes 18, 19, 12, 14, 16, 22 are selected by software running on computer system 20, which couples these electrodes 18, 19, 12, 14, 16, 22 to the signal generator 25. A pair of electrodes, for example electrodes 18 and 19, may be excited by the signal generator 25 and they generate a field in the body of the patient and the heart 10. During the delivery of the current pulse, the remaining patch electrodes 12, 14, 16, 22 are referenced to the belly patch electrode 21, and the voltages impressed on these remaining electrodes 12, 14, 16, 22 are measured by the analog-to-digital or A-to-D converter 26. Suitable lowpass filtering of the digital data may be subsequently performed in software to remove electronic noise and cardiac motion artifact after suitable low pass filtering in filter 27. In this fashion, the various patch electrodes 18, 19, 12, 14, 16, 22 are divided into driven and non-driven electrode sets. While a pair of electrodes is driven by the signal generator 25, the remaining non-driven electrodes are used as references to synthesize the orthogonal drive axes.

The belly patch electrode 21 is seen in the figure is an alternative to a fixed intra-cardiac electrode. In many instances, a coronary sinus electrode or other fixed electrode in the heart 10 can be used as a reference for measuring voltages and displacements. All of the raw patch voltage data is measured by the A-to-D converter 26 and stored in the computer system 20 under the direction of software. This electrode excitation process occurs rapidly and sequentially as alternate sets of patch electrodes 18, 19, 12, 14, 16, 22 are selected, and the remaining members of the set are used to measure voltages. This collection of voltage measurements may be referred to herein as the "patch data set". The software has access to each individual voltage measurement made at each individual patch electrode 18, 19, 12, 14, 16, 22 during each excitation of each pair of electrodes 18, 19, 12, 14, 16, 22.

The raw patch data is used to determine the "raw" location in three spaces (X, Y, Z) of the electrodes inside the heart 10, such as the roving electrodes 17. The patch data set may also be used to create a respiration compensation value to improve the raw location data for the locations of the electrodes 18, 19, 12, 14, 16, 22.

If the roving electrodes 17 are swept around in the heart chamber while the heart 10 is beating, a large number of electrode locations are collected. These data points are taken at all stages of the heartbeat and without regard to the cardiac phase. Since the heart 10 changes shape during contraction, only a small number of the points represent the maximum heart volume. By selecting the most exterior points, it is possible to create a "shell" representing the shape of the heart 10. The location attribute of the electrodes within the heart 10 are measured while the electric field is impressed on the heart 10 by the surface patch electrodes 18, 19, 12, 14, 16, 22.

Figure 2:
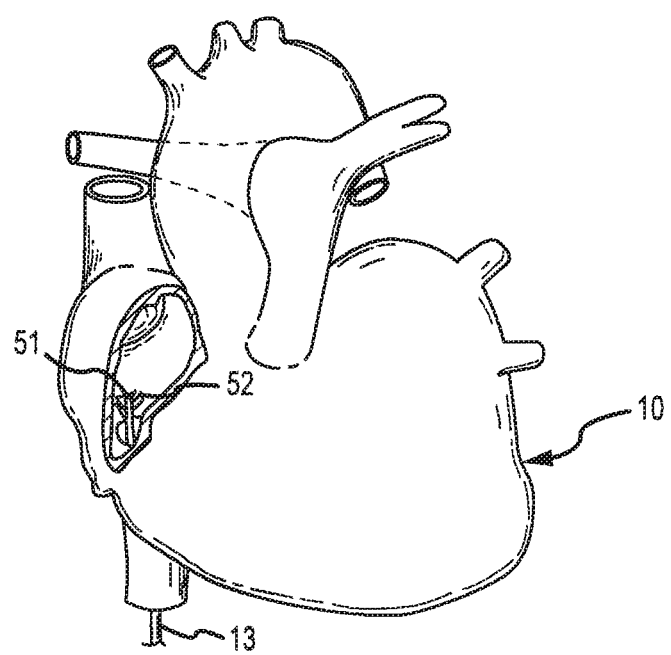
FIG. 2 illustrates a catheter constructed in accordance with the present invention being introduced into a patient's heart.

FIG. 2 shows a catheter 13, which may be a high-density mapping catheter, as described in more detail below, in the heart 10. The catheter 13 has a tip electrode 51 and additional electrodes 52. Since these electrodes 51 and 52 lie in the heart 10, the location process detects their location in the heart 10. While they lie on the surface and when the signal generator 25 is "off", each patch electrode 18, 19, 12, 14, 16, 22 (FIG. 1) can be used to measure the voltage on the heart surface. The magnitude of this voltage, as well as the timing relationship of the signal with respect to the heartbeat events, may be measured and presented to the cardiologist through the display 23. The peak-to-peak voltage measured at a particular location on the heart wall is capable of showing areas of diminished conductivity, and which may reflect an infracted region of the heart 10. The timing relationship data are typically displayed as "isochrones". In essence, regions that receive the depolarization waveform at the same time are shown in the same false color or gray scale.

Figure 3:
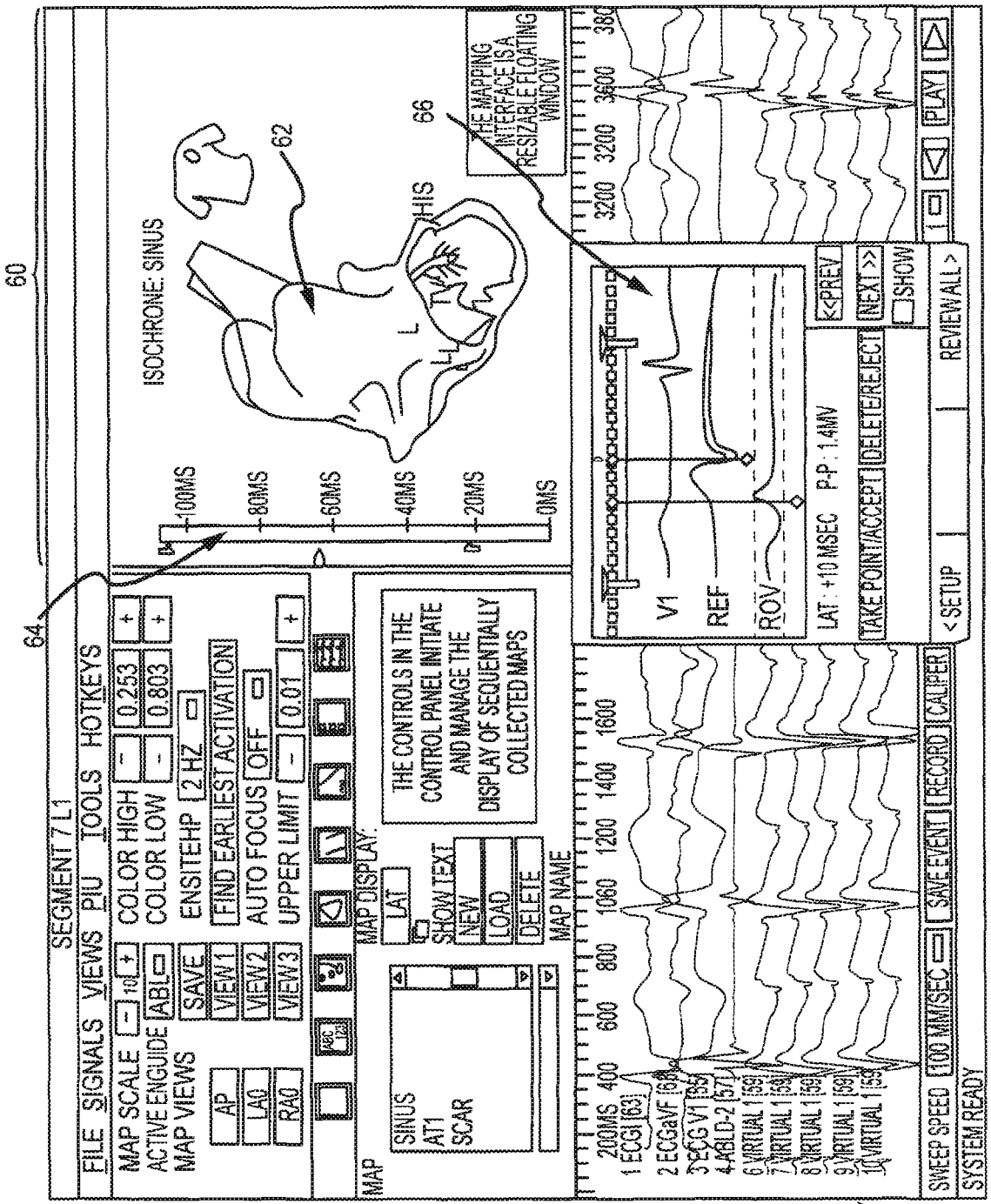
FIG. 3 illustrates a display provided by a navigation and mapping system in accordance with the present invention.

FIG. 3 shows an illustrative computer display from the computer system 20. The display 23 is used to show data to the physician user and to present certain options that allow the user to tailor the system configuration for a particular use. It should be noted that the contents on the display 23 can be easily modified and the specific data presented is only of a representative nature. An image panel 60 shows a geometry of the heart chamber 62 that shows "isochrones" in false color or grayscale together with guide bar 64 to assist in interpretation. In this hypothetical image, the noted mapping methodology has been used with a high-density catheter to create a chamber representation that is displayed as a contoured image.

The guide bar 64 is graduated in milliseconds and it shows the assignment of time relationship for the false color image in the geometry. The relationship between the false color on the geometry image 62 and the guide bar 64 is defined by interaction with the user in panel 66. As shown, the display may also provide traces and other information related to the ECG electrodes, mapping electrodes and reference electrodes, as well as other information that may assist the physicians.

Figure 5A:
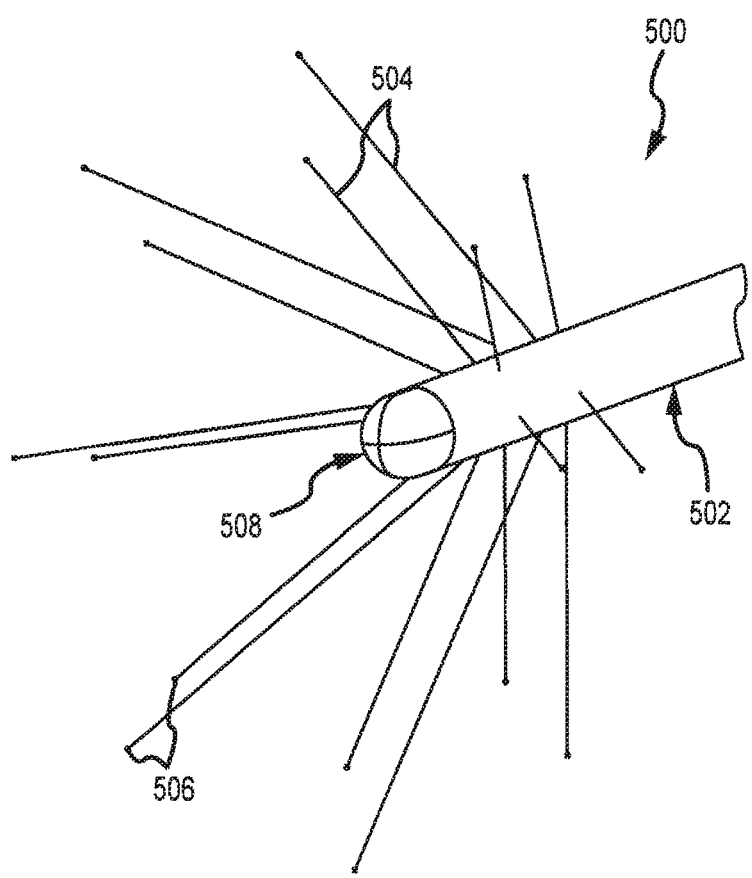
Figure 5B:
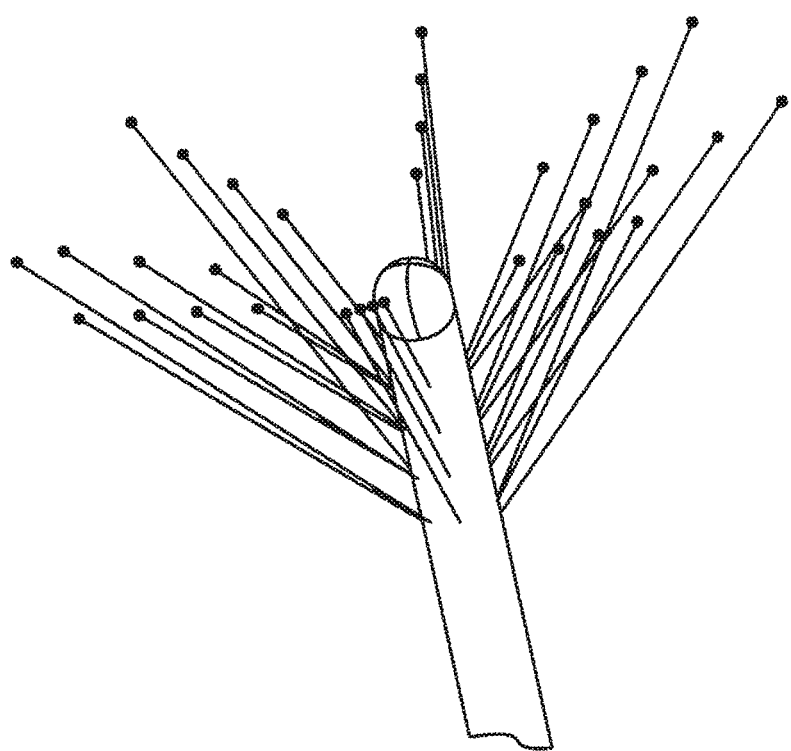

As noted above, a significant amount of data is required to generate a detailed image of the cardiac tissue of interest. In order to gather adequate data more quickly, it is desirable to provide a high density mapping electrode catheter having a plurality of electrodes. Once such catheter in accordance with the present invention is illustrated in FIGS. 5A and 5B. The illustrated catheter 500 includes a catheter body or shaft 502 having an electrode tip 508 disposed at a distal end thereof. The catheter 500 further includes a number of mapping electrode fibers 504 extending from the catheter shaft 502. Each of the illustrated mapping electrode fibers 504 terminates in a tip electrode 506. The electrodes 506 and 508 can be used to map cardiac tissue, as discussed above. More specifically, a physician can sweep the electrodes 506 and 508 across tissue to be mapped. In this regard, a large volume of mapping information can be obtained quickly due to the large number of electrodes 506 and 508 that can be maintained in contact with the tissue as the catheter 500 is swept across the tissue.

As will be described in more detail below, each of the mapping electrode fibers 504 may be formed from a shape memory fiber with a conductive core. For example, the fibers may be formed from a nickel titanium shaped memory fiber such as Nitinol with a conductive metallic core such as platinum. In addition, the fibers may be coated with an insulating material, e.g., Polyimide, to prevent shorts. The conductive core of the illustrated fibers 504 serves as the electrical pathway for the tip electrodes 506. In addition, the tip electrodes 506 may be formed, as discussed below, by melting an exposed section of the conductive core. Alternatively, the tip electrodes may be formed separately and then tightly secured to the fibers.

Each of the electrode fibers 504 may be threaded through an inner lumen of the catheter shaft 502. The fibers 504 then extend through holes formed in the catheter shaft 502 at the desired location. As is well known, shape memory materials such as Nitinol can be processed to remember a desired shape. When the shape memory materials are deflected from this remembered shape, the shape memory properties of the material tend to return the material to the remembered shape. In this case, the fibers 504 are processed to extend outwardly and forwardly from the catheter shift when unconstrained. The fibers may be bonded to the shaft 502 at the openings or may be maintained in a substantially fixed relationship with respect to the shaft 502 due to the configuration of the fibers 504. In one construction implementation, platinum core Nitinol fibers with a Polyimide coating are threaded through the inner lumen of the catheter shaft 502. The distal ends of the fibers are then pulled through openings in the catheter shaft, and a desired length of the fiber is pulled through the opening. The fibers are then processed to remember a particular configuration in relation to the angle formed between the catheter shaft 502 and the extending fibers 504, as will be discussed in more detail below. Thereafter, a first length of the Polyimide coating and a second length of the Nitinol material are stripped from the end of the fibers to expose a portion of the platinum core. This platinum core is then melted to form a general spherical electrode tip 508. It will be appreciated that other production sequences are possible. For example, the electrodes need not be integrally formed.

Generally, the catheter shaft 502 will have a diameter and stiffness that is significantly greater than the diameter and stiffness of the individual fibers 504. For instance, the catheter shaft 502 may be a 5 or 7 French (i.e., 0.065 in. or 0.092 in.) catheter. In such embodiments, the catheter shaft may have a diameter that is at least five to ten times (or more) the diameter of the individual fibers. Such a difference in the relative sizes of the fibers 504 and the catheter shaft 502 may allow the fibers 504 to readily deflect when they are moved (e.g., brushed) over an internal tissue surface without significant deflection of the catheter shaft. For instance, each individual fiber may have a buckle strength (e.g., where bending is initiated) of no more than about 5 grams and more preferably no more than about 1-2 grams. Use of such low buckling strength allows the ends of the fibers 504 to readily conform to a tissue surface without significantly deflecting or otherwise penetrating the tissue surface. In contrast, when the catheter shaft contacts such an internal tissue surface, the stiffness of the shaft alerts an operator (e.g., physician) that the catheter shaft is in contact with patient tissue.

The inner lumen of the catheter shaft 502 may also be used to thread wiring for the tip electrode 508. In addition, for certain procedures, it may be desired to irrigate the electrodes 506 and/or 508 with saline solution, for example, to prevent undesired heating or clotting. A lumen for such irrigation fluid may be formed within catheter shaft 502 (which can include openings to allow for flow of the irrigation fluid), or the irrigation fluid may be delivered via a separate lumen associated with other structure of the catheter.

Figure 4:
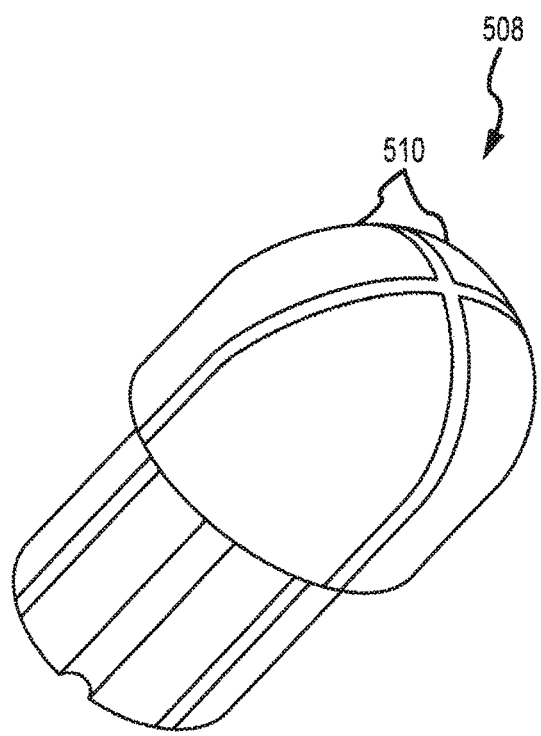
FIGS. 4-6F illustrate various embodiments of a high density mapping catheter in accordance with the present invention.

The tip electrode 508 can be any of various types of electrode tips including an ablation tip or a mapping tip. The illustrated electrode tip 508 is a mapping tip, as best shown in FIG. 4. The mapping tip 508 is divided into a number of electrically isolated sections 510, in this case, defining four quadrants. Because the sections 510 are electrically isolated, independent positioning signals can be obtained with regard to each of the sections 510. In this manner the signals from the sections 510 can be processed to define references, e.g., North, South, East and West, which are useful in guiding movement of the catheter during a medical procedure. It will be appreciated in this regard that it may be useful to press the catheter tip directly into cardiac tissue in a head-on configuration. In this regard, it is advantageous to configure the electrode fibers 504 in a forwardly extending configuration, as illustrated in FIGS. 5A and 5B, so as to obtain positioning data from a number of electrodes that are circumferentially disposed in relation to the tip electrode 508. Similar advantages are obtained in relation to guidance of the tip electrode in ablation applications.

Figure 6A:
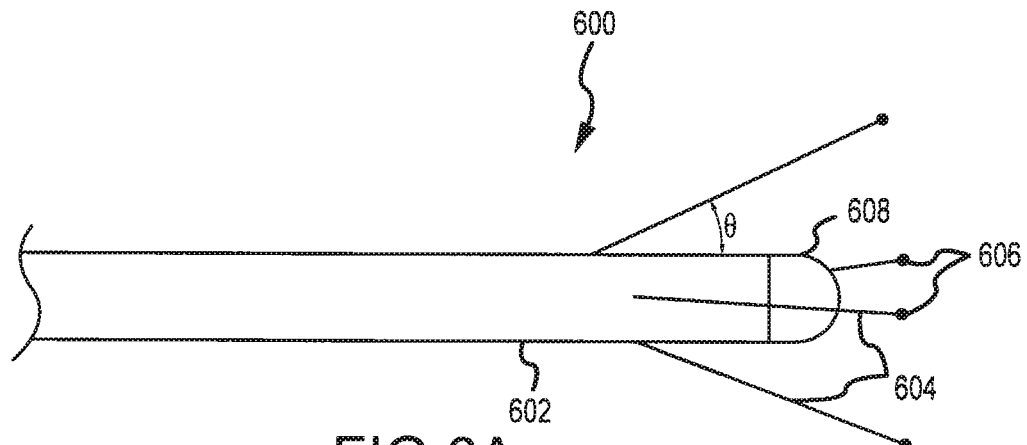

While the catheter 500 of FIGS. 4-5B thus represents an advantageous implementation of the present invention, it will be appreciated that many other implementations are possible. Some examples in this regard are illustrated in FIGS. 6B-6F. Referring first to FIG. 6A, the illustrated catheter 600 includes a catheter shaft 602 having an electrode tip 608 at a distal end thereof. In this case, the catheter 600 includes four mapping electrode fibers 604 formed from conductive core shape memory fibers, as described above. When unconstrained, each of the electrode fibers 604 extends outwardly and forwardly from the catheter shaft 602 so as to define an angle θ therebetween. A number of factors may be considered in determining a value of θ for a particular application. Some of these factors include the following:

1. The angle θ may be selected to provide a desired lateral spacing of the electrode tips 606 for a given length of the electrode fibers 604 extending from the shaft 602;

2. The angle θ is preferably greater than zero but less than 90 degrees in order to provide the desired forwardly extending configuration; and 3. The angle θ may be selected to allow the fibers 604 to be retracted within a sheath and extended therefrom without undue resistance or stress on the fibers 604.

It will be appreciated that other factors may be considered in this regard. In the illustrated embodiment, the angle θ is preferably between about 30 degrees and 60 degrees, for example, about 45 degrees. It will be appreciated that different angles may be used for different fibers if desired.

Figure 6B:
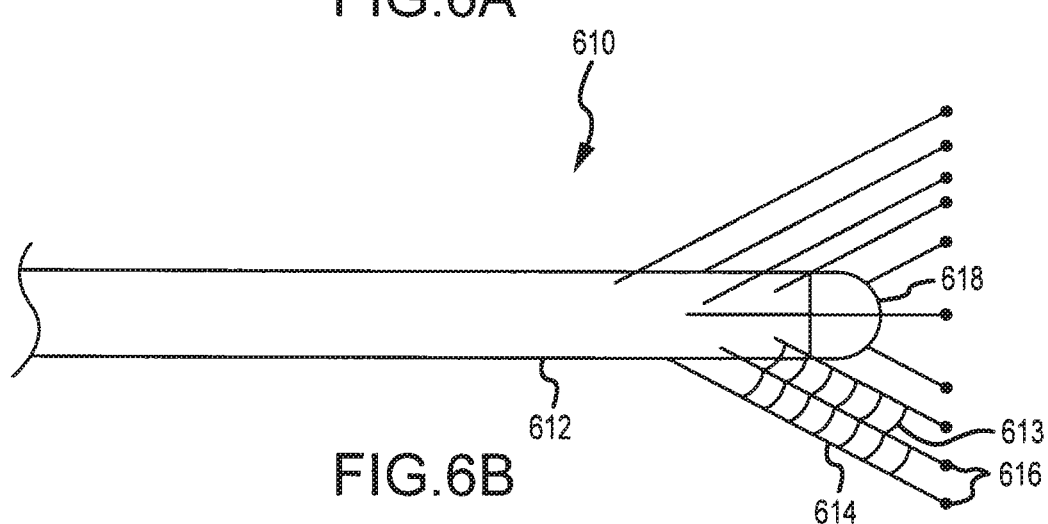

FIG. 6B shows an embodiment of a catheter 610 where a larger number of fibers 614 extend from the catheter shaft 612. In addition, the illustrated fibers 614 are configured in a number of rows at different distances from the distal end of the shaft 612. The fibers 614 in adjacent rows may be staggered so as to reduce the likelihood of shorts due to contact between electrode tips 616S. In the embodiment of FIG. 6B (as well as that of FIG. 6A), the tip electrodes 616 are arranged in a generally planar configuration slightly forward of the tip electrode 618 when unconstrained. It will thus be appreciated that the fibers 614 of different rows have different lengths. Such a configuration may be desirable in order to promote good contact by as many tip electrodes 616 as possible in relation to a head-on approach to cardiac tissue. That is, in connection with axial advancement of the shaft 612 towards cardiac tissue, it is expected that the tip electrodes 616 will first come into contact with the tissue. As advancement of the shaft 612 progresses, the fibers 616 deflect slightly to allow contact of the tip electrode with the tissue. Due to the shape memory properties of the fibers 614, the tip electrode 616 will then be urged into good contact with the tissue and can accommodate a range of tissue contours. In addition, FIG. 6B also shows use of an optional webbing 613 that extends between adjacent fibers. Such webbing may be formed of a thin elastomeric material and provides a redundancy means for retaining an electrode fiber connected to the catheter shaft 612 in the event that the proximal end of the fiber 614 were to become disconnected from the catheter shaft 612.

Figure 6C:
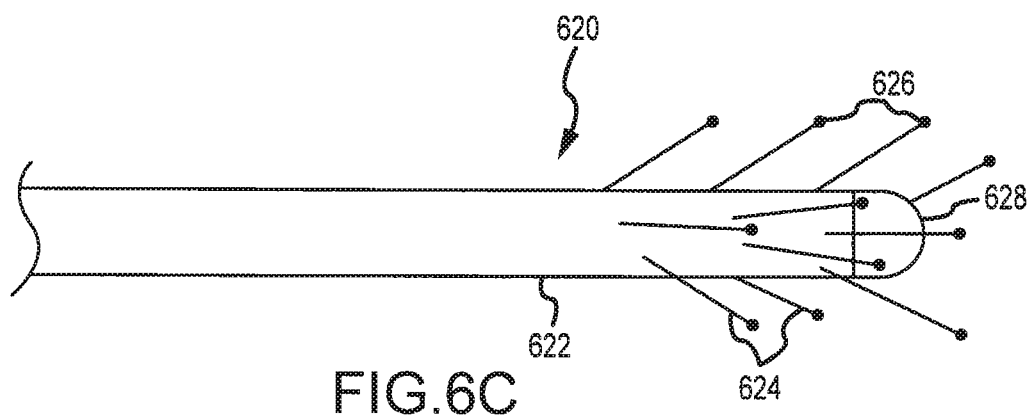

FIG. 6C shows a further alternative embodiment of a catheter 620 in accordance with the present invention. In this case, a number of electrode fibers 624 extend from the catheter shaft 622 at different positions along the length of the catheter shaft 622. Again, fibers 624 of adjacent rows may be staggered, as discussed above. However, in this case, the tip electrodes 626 do not define a planar configuration. Rather, some of the tip electrodes 626 extend beyond the tip electrode 628 of the catheter shaft 622, but others do not. Thus, the illustrated catheter 620 provides good mapping electrode contact for head-on approaches to cardiac tissue but also provides good contact in cases of dragging the catheter 620 across cardiac tissue with a side surface of the shaft 622 laying on the cardiac tissue as may be desired or otherwise occur. Moreover, in this configuration, there is a reduced likelihood of shorts due to contact between electrode tips 626. It should be noted that any such shorts are not hazardous as the tip electrodes 626 are essentially receiving electrodes. Moreover, such shorts can be readily recognized and disregarded by the mapping processing logic. Nonetheless, avoiding such shorts enhances the amount of data that can be acquired.

Figure 6D:
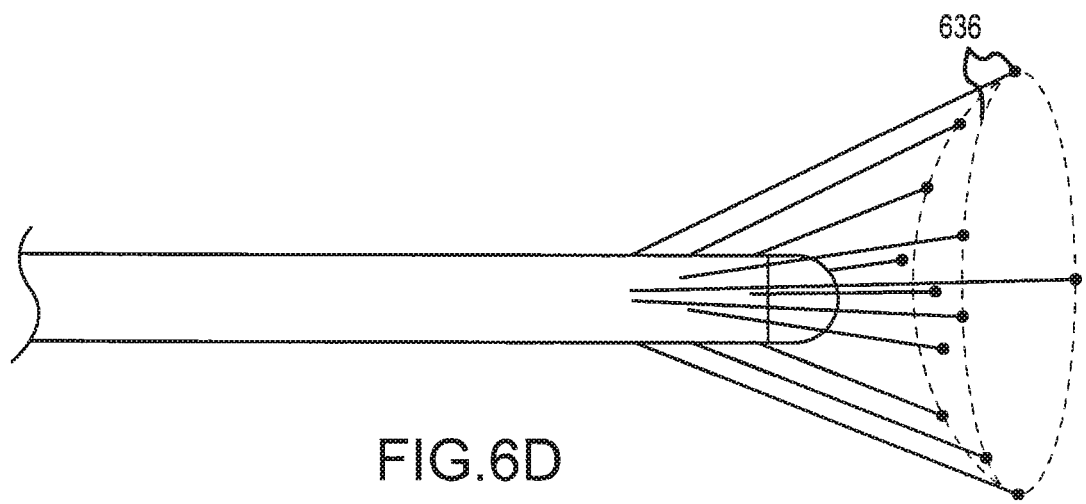
Figure 6E:
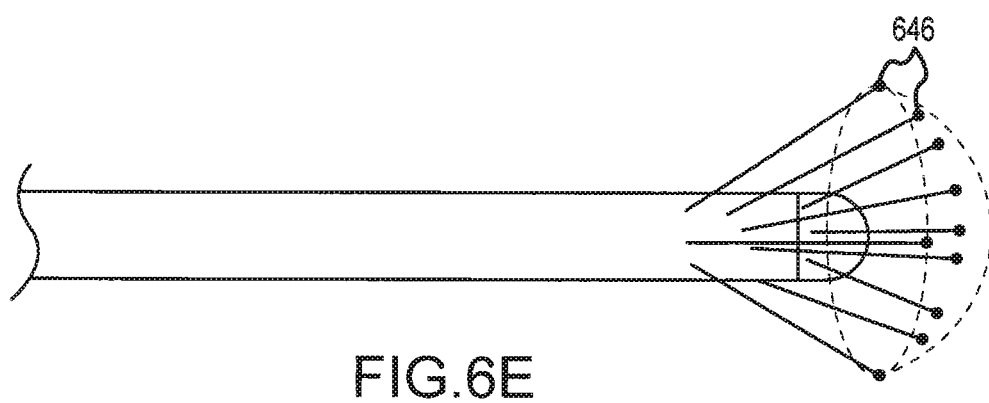

In certain embodiments described above, the mapping tip electrodes were shown and described as defining a planar configuration when unconstrained. In some cases, a different special configuration may be desired. For example, when the catheter is expected to be deployed against a concave cardiac wall surface, a complementary spatial configuration (i.e., convex) of the tip electrodes may be desired. Conversely, when it is expected that the catheter will be deployed against a convex surface, a concave special configuration of the tip electrodes may be desired. FIGS. 6D and 6E illustrate concave and convex configurations of the tip electrodes 636 and 646 in this regard.

Figure 6F:
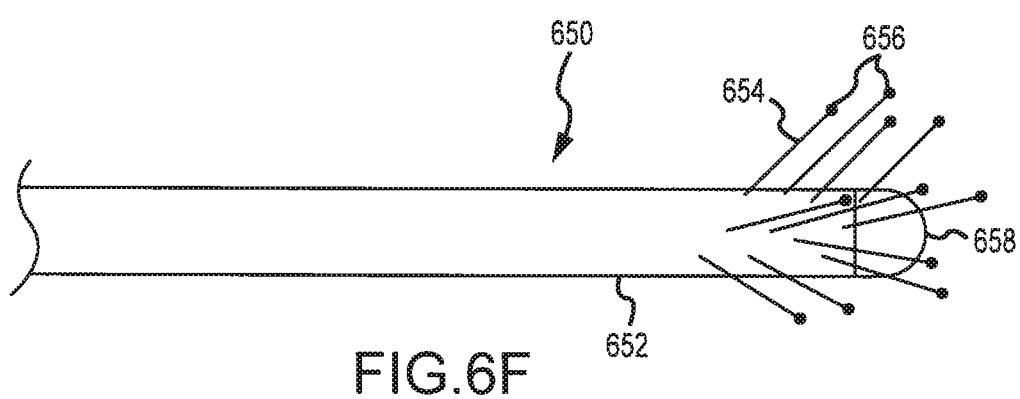

In connection with certain embodiments above, the mapping electrode fibers have been described as being configured in rows in relation to the length of the catheter shaft. It will be appreciated that it is unnecessary to deploy the electrode fibers in rows. This is illustrated in FIG. 6F. There, the illustrated catheter 650 includes a number of electrode fibers 654 terminating in fiber end 656. The illustrated fibers 654 extend from the catheter shaft 652 at various locations along the shaft 652, but they are not arranged in rows defined by a common location along the length of the shaft 652. Similar to certain embodiments above, some of the tip electrodes 656 extend beyond the tip electrode 658, but others do not. Moreover, different ones of the fibers 654 may extend different lengths from the shaft 652.

Figure 9A:
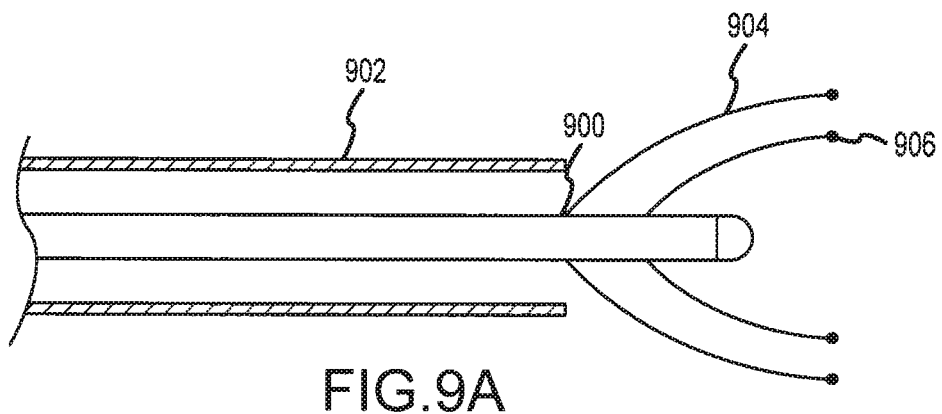
FIGS. 9A-9C show a high density mapping catheter with curved electrode fibers in accordance with the present invention.
Figure 9B:
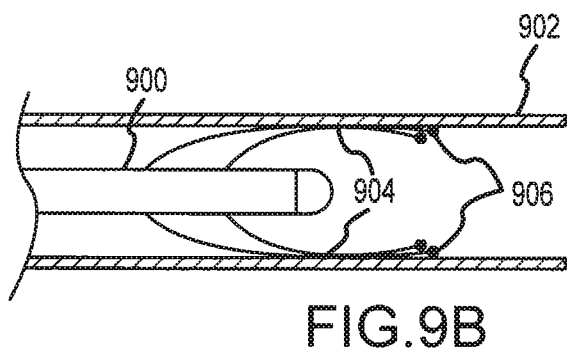
Figure 9C:
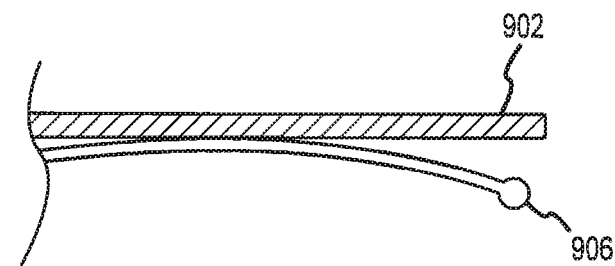

As a further alternative, the electrode fibers may be cured rather than straight. This is generally shown in FIGS. 9A-9C. The illustrated catheter includes a core 900 with a number of curved electrode fibers 904 extending therefrom. Each of the electrode fibers 904 terminates in a tip electrode 9-6 as discussed above. The catheter is delivered to the procedure site in an introducer or sheath 902.

In the illustrated embodiment, each of the electrode fibers 904 has a slightly convex curve. When the core 900 is retracted into the sheath 902, as shown in section 9B, the tip electrodes extend inwardly from the sheath 902. This is best seen in the enlarged view of FIG. 9C. This reduces concerns about the enlarged tip electrode 906 snagging on the end of the sheath 902.

Figure 7A:
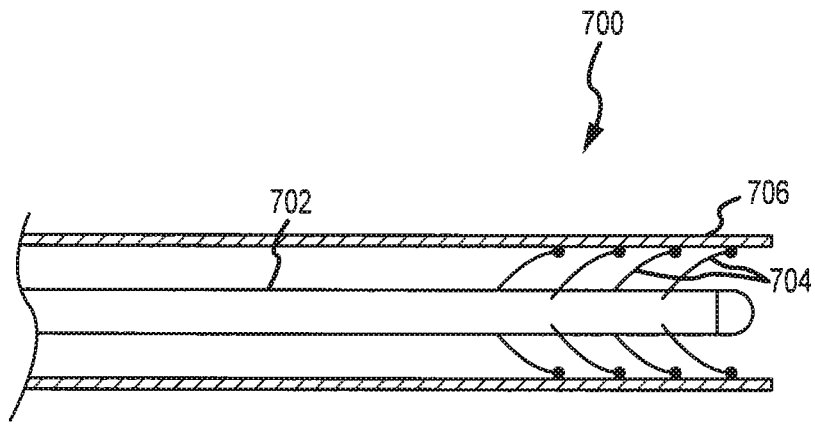
FIGS. 7A-7C illustrate operation of a high density mapping catheter in accordance with the present invention.
Figure 7B:
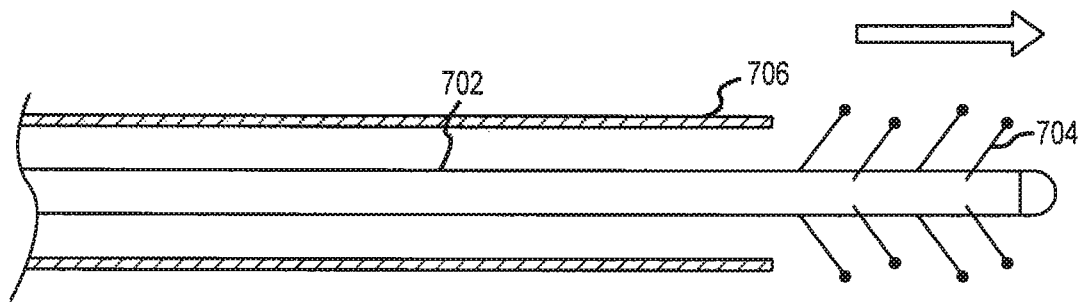

As discussed above, the electrode fibers preferably extend outwardly and forwardly in relation to the catheter shaft. A number of advantages associated with this geometry were noted above. A further advantage is illustrated with reference to FIGS. 7A-7C, which also illustrate the operation of the mapping catheter. As shown in FIG. 7A, as the catheter 700 is threaded through a vessel of a patient to the patient's heart, the catheter shaft 702 and electrode fibers 704 may be in a retracted configuration in relation to a sheath 706. It will be appreciated that this provides a compact profile, which facilitates passage of the catheter through the patient's vessel. Once the catheter has reached the desired site for medical procedure, the catheter shaft 702 can be advanced in relation to the sheath 706, as shown in FIG. 7B.

Figure 7C:
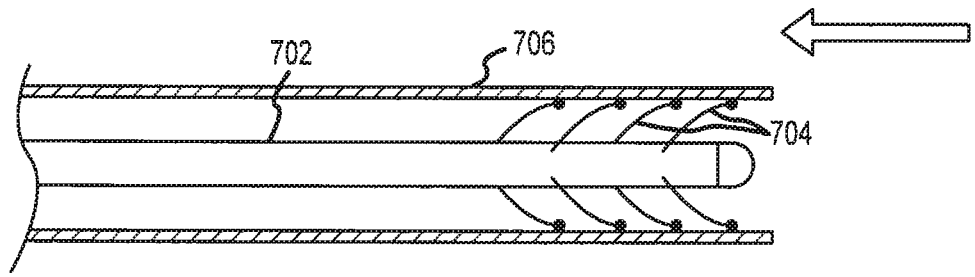

Once the electrode fibers 704 extend beyond the end of the sheath 706 and are unconstrained, they spring into the deployed configuration due to the operation of the shape memory alloy. When the procedure is completed, the catheter shaft 702 can be retracted back into the sheath 706, as shown in FIG. 7C. As this occurs, the electrode fibers 704 deflect and are constrained by the sheath 706. It will be appreciated that the forwardly extending configuration of the fibers 704 facilitates the deployment and retraction of the catheter shaft 702, as shown in FIGS. 7A-7C. In particular, the forwardly extending configuration reduces the resistance of the fibers to retraction of the shaft 702. Moreover, the angular range of deflection associated with advancement and withdraw of the shaft 702 in relation to the sheath 706 is minimized. This reduces stress to the fibers 704.

Figure 8A:
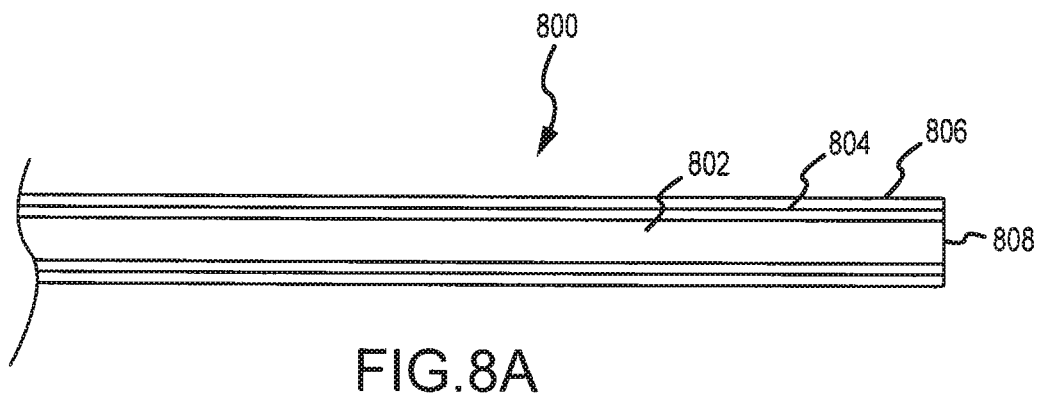
FIGS. 8A-8C illustrate construction of an electrode fiber for use in a high density mapping catheter in accordance with the present invention.
Figure 8B:
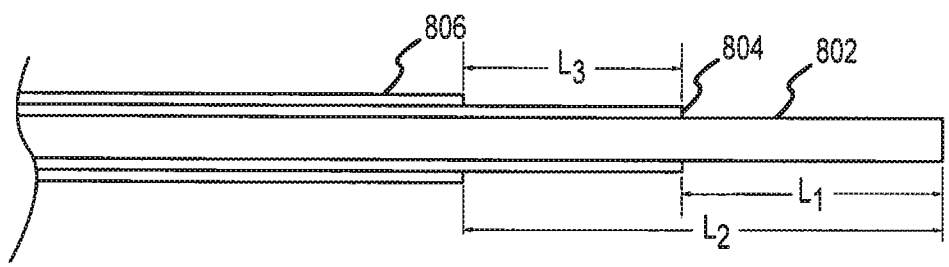
Figure 8C:
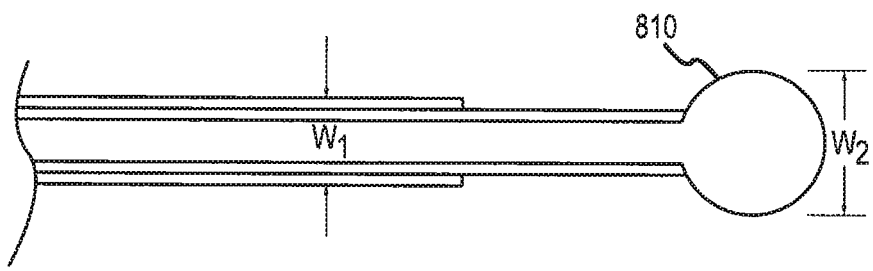

FIGS. 8A-8C illustrate a process for forming an electrode fiber as utilized in the various embodiments described above. In particular, it is desirable to provide an enlarged, generally spherical tip electrode in connection with the electrode fibers. This tip electrode configuration has a number of advantages. First, it is desirable to avoid puncturing of the cardiac tissue in connection with contact by the mapping electrodes. The enlarged and rounded configuration of the tip electrodes in this regard provides a larger surface contact area and reduces the pressure on and likelihood of puncturing any cardiac tissue contacted. In addition, it is desirable to enhance the visibility of the tip electrodes, both on the mapping display and in connection with any fluoroscopic images obtained in connection with the procedure. The enlarged tip electrode improves impedance and, therefore, visibility with respect to the electrical navigation system. The increased cross-section also improves visibility with respect to the fluoroscopic images.

Referring to FIGS. 8A-8C, the electrode fibers may be formed from commercially available conductive core shape memory fibers. For example, the electrode fibers may be formed from platinum core nickel titanium fibers. Such a commercially available fiber is illustrated in FIG. 8A. The fiber 800 includes a conductive core 802 that may be formed, for example, from a metallic conductor such as platinum. The core is surrounded by a tube of shape memory alloy material 804 such as a nickel-titanium material. An insulating coating 806 may be provided around the shape memory alloy 804 (which is also conductive).

To form the electrode fiber, the shape memory alloy material 804 and insulative coating 806 are stripped back from the distal end 808 of the fiber 800. More specifically, the shape memory material is stripped back a distance $L_1$, and the insulating coating 806 is striped back a distance $L_2$ that is greater than the distance $L_1$. This leaves a length of $L_3$ where the shape memory material 804 is exposed. In one embodiment, the distance $L_3$ is between about 0.020 and 0.060 of an inch, for example, 0.040 of an inch.

The exposed core 802 is then melted to form a generally spherical tip electrode 810, as shown in FIG. 8C. For example, a laser may be used to melt the core, or the core may be exposed to another heat source. The result is a tip electrode 8110 that has a diameter or width $w_2$ that is greater than the width $w_1$ of the fiber 800. In this regard, the fiber preferably has a width $w_1$ of between about 0.002 to 0.006 of an inch, for example, 0.002 of an inch. The tip electrode 810 has a width $w_2$ of between about 0.003 and 0.012 of an inch, for example, 0.006 of an inch. This fiber, in combination with the geometries described above, provides a suitable stiffness or resistance to retraction of the catheter shaft into the sheath. That is, there is not undue resistance or stress on the electrode fibers.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A catheter for use in electrical mapping of internal tissue, comprising:
    a sheath;
    a catheter body comprising a distal tip and a proximal portion, said catheter body defining a longitudinal axis, wherein said catheter body is movable relative to said sheath between a retracted position within said sheath and an extended position where said distal tip and a sidewall portion of said catheter extend beyond a distal end of said sheath;
    a plurality of fibers each comprising a first end fixedly connected to said sidewall portion of said catheter body and a second free end, wherein, in an unconstrained state in said extended position, free ends of said fibers extend outward from said sidewall portion of said catheter body and forwardly in the distal direction, wherein each of said plurality of fibers comprises:
    a shape memory alloy tube comprising a conductive core disposed within an interior of said shape memory alloy tube, wherein said shape memory alloy tube is conformally disposed in direct contact with an outside surface of said conductive core and surrounds said conductive core, wherein said conductive core and said shape memory alloy tube are comprised of first and second different materials; and
    a tip electrode, supported on said free end of said fiber, wherein said conductive core functions as an electrical pathway for said tip electrode.

2. The catheter of claim 1, wherein in an uncontstrained state each of said fibers comprises an elongated element having a free distal end and a proximal end attached to said sidewall portion of said catheter body, wherein an angle between a long axis of said elongated element and said longitudinal axis is acute.

3. The catheter of claim 2, wherein said acute angle is between 30 degrees and 60 degrees.

4. The catheter of claim 1, wherein distal ends of at least a portion of said fibers extend to an axial location beyond said distal tip of said catheter body.

5. The catheter of claim 4, wherein all distal ends of said fibers extend beyond said distal tip of said catheter body.

6. The catheter of claim 5, wherein all of said distal ends are disposed in a substantially common plane.

7. The catheter of claim 1, wherein said tip electrode is integrally formed with said conductive core.

8. The catheter of claim 1, wherein a diameter of said catheter body is at least five (5) times the diameter of each individual fiber of said plurality of fibers.

9. The catheter of claim 1, wherein a diameter of each individual fiber of said plurality of fibers is no greater than 0.006 inches.

10. The catheter of claim 1, wherein a diameter of said tip electrode is greater than a diameter of said individual fiber.

11. The catheter of claim 1, wherein a buckling force required to bend each individual fiber of said plurality of fiber is no greater than 2 grams.

12. The catheter of claim 1, wherein at least first and second fibers of said plurality of fibers have different lengths.

13. The catheter of claim 1, wherein said plurality of fibers are disposed about a circumference of said catheter body.

14. The catheter of claim 13, wherein said plurality of fibers are axially disposed at different locations along a length of said catheter body.

15. The catheter of claim 13, wherein said plurality of fibers are linearly aligned in at least three axial rows disposed about said circumference of said catheter.

16. The catheter of claim 1, further comprising:
    a catheter tip electrode disposed on the distal tip of said catheter body.

17. The catheter of claim 16, wherein said catheter tip electrode comprises at least first and second electronically isolated sections.

18. A catheter for use in electrical mapping of internal tissue, comprising:
    a sheath;
    a catheter body extending between a distal tip and a proximal portion, said catheter body defining a longitudinal axis, wherein said catheter body is movable relative to said sheath between a retracted position within said sheath and an extended position where said distal tip and a sidewall portion of said catheter body extend beyond a distal end of said sheath;
    a plurality of curved fibers extending from said sidewall portion of said catheter body, each of said curved fibers having a curved body that extends between a fiber base proximate to said sidewall portion and a free distal end and that curve toward a central axis of said catheter body, and wherein each of said curved fibers comprises a conductive core conformally disposed within an interior of a shape memory alloy tube that is disposed directly on and surrounds an outside surface of the conductive core and an insulative covering disposed on an exterior surface of said shape memory alloy tube;

a mapping electrode, supported on said free distal end at least one of said plurality of curved fibers, for use in acquiring mapping information, wherein said conductive core functions as an electrical pathway for said mapping electrode and wherein said mapping electrode has a generally spherical shape having a width that is greater than a width of said one curved fiber;

wherein, in said retracted position, said curved body of said at least one of said plurality of curved fibers is sized to contact an inside surface of said sheath between its base and free distal end to maintain said mapping electrode inward from said sheath.

19. The catheter of claim 18, wherein in said extended position said free distal ends of said plurality of fibers extend distally forward beyond said distal tip of said catheter body.

20. The catheter of claim 1, wherein, in said retracted position, said plurality of fibers are compressed between said sidewall of said catheter body and an inside surface of said sheath.

21. The catheter of claim 18, wherein said curved body of said at least one of said plurality of curved fibers is sized to maintain said mapping electrode at a distance away from said sheath that is greater than one-half of the width of said mapping electrode.

22. The catheter of claim 16, wherein in the unconstrained state in said extended position, said free ends of said plurality of fibers extend distally forward beyond said tip electrode disposed on the distal tip of said catheter body.

23. The catheter if claim 19, wherein said distal tip of said catheter body further comprises a tip electrode, wherein said free distal ends of said plurality of fibers extend distally forward beyond said tip electrode.

* * * * *